(12) United States Patent
Unger et al.

(10) Patent No.: US 6,418,334 B1  
(45) Date of Patent: Jul. 9, 2002

(54) METHOD AND APPARATUS FOR LOGGING AND DYNAMICALLY CONFIGURING PERFORMANCE ANALYSIS OF A MEDICAL DIAGNOSTIC IMAGING SYSTEM

(75) Inventors: Christopher David Unger, Delafield; Frank Willard Childress, Brookfield, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/420,924

(22) Filed: Oct. 19, 1999

(51) Int. Cl.⁷ ............................................ A61B 5/05
(52) U.S. Cl. ................... 600/407; 128/922; 382/128
(58) Field of Search ............................ 600/407, 410, 600/425, 437, 438; 382/128; 128/920, 922, 923, 925; 705/3; 378/901

(56) References Cited

U.S. PATENT DOCUMENTS

| | | | |
|---|---|---|---|
| 5,447,153 A | * 9/1995 | Weil et al. | 600/300 |
| 5,619,995 A | * 4/1997 | Lobodzinski | 348/77 |
| 5,781,442 A | * 7/1998 | Engleson et al. | 700/214 |
| 6,101,407 A | * 8/2000 | Groezinger | 600/407 |
| 6,201,900 B1 | * 3/2001 | Hossack et al. | 348/441 |
| 6,289,115 B1 | * 9/2001 | Takeo | 128/920 |
| 6,356,780 B1 | * 3/2002 | Licato et al. | 382/128 |

* cited by examiner

Primary Examiner—Marvin M. Lateef  
Assistant Examiner—Eleni Mantis Mercader  
(74) Attorney, Agent, or Firm—McAndrews, Held & Malloy, Ltd.; Peter J. Vogel; Michael A. Dellapenna (57) ABSTRACT

A method and apparatus are provided for configurable logging and analysis of performance data for a medical diagnostic imaging system. A medical diagnostic imaging system may be divided into at least one subsystem. The subsystems include data acquisition modules for acquiring desired types of data related to the performance of an associated subsystem. The data acquisition modules acquire raw performance data during the operation of the medical diagnostic imaging system. The data acquisition modules may remotely acquire the raw performance data. The raw performance data may be acquired based upon a configuration file which identifies parameters associated with a desired type of performance analysis. New configuration files may be downloaded to dynamically select at least one parameter for a desired type of performance analysis. Parameters in the configuration file may comprise at least one of a performance variable and a sampling rate for the performance variable. A processing module processes the raw performance data acquired by the data acquisition modules. Data may be processed in real-time during the operation of the medical diagnostic imaging system. The processing module produces characteristic data summarizing the raw performance data. For example, the processing module may calculate trend statistics or perform statistical analyze on the raw performance data to produce characteristic data.

49 Claims, 5 Drawing Sheets

METHOD AND APPARATUS FOR LOGGING AND DYNAMICALLY CONFIGURING PERFORMANCE ANALYSIS OF A MEDICAL DIAGNOSTIC IMAGING SYSTEM

CROSS REFERENCE TO RELATED APPLICATIONS (if applicable)

NOT APPLICABLE.

STATEMENT REGARDING FEDERALLY SPONSORED RESEARCH & DEVELOPMENT (if applicable)

NOT APPLICABLE.

BACKGROUND OF THE INVENTION

The present invention generally relates to a system for logging and analyzing medical diagnostic imaging system data. More particularly, the present invention relates to a system for logging and dynamically configuring performance analysis of medical diagnostic imaging system data, such as for six sigma studies.

The information gained from diagnostic imaging has applications in many fields, including medicine and manufacturing. Medical diagnostic imaging systems, such as an x-ray system, ultrasound system, magnetic resonance imaging (MRI) system, computed axial tomography (CAT) system, and the like, typically include a source and a detector. A target to be viewed, such as a human body, is arranged between the source and the detector. The source transmits a medium that travels through the target to reach the detector. As the medium travels from the source through the target, internal components of the target may affect the medium, such as by decreasing the energy of the medium to varying degrees through phenomena such as the blocking or absorption of the medium. The blocking or absorption of a medium, such as x-rays, within the target causes the received energy levels to vary. The detector receives the energy which have traveled through, or is reflected from, the target. An image of the target is generated based on the energy detected at the detector. The produced image contains light and dark regions which correspond to the varying intensity levels of the energy that passed through, or were reflected by, the target.

Medical diagnostic images produced by the above-described general types of system may be used for many purposes. For instance, internal defects in the target may be detected. Additionally, changes in internal structure or alignment may be determined. Furthermore, the image may show the presence or absence of objects in the target.

In order to help ensure that medical diagnostic images may be used reliably, it is advantageous to measure and verify the performance of a medical diagnostic imaging system. In particular, it is important to measure and verify the image quality of the medical diagnostic imaging system. Poor image quality may prevent reliable analysis of the medical diagnostic image. For example, a decrease in image contrast quality may yield an unreliable image that is not usable. Additionally, the advent of real-time imaging systems has increased the importance of generating clear, high quality images. Medical diagnostic imaging systems with poor or degraded image quality must be re-calibrated to provide a distinct and usable representation of the target.

It is also important to verify performance of a medical diagnostic imaging system for safety reasons. For example, exposure to high levels of energy may involve some health risk to humans. Because of the health risk, governmental standards are set for the use of certain medical diagnostic imaging systems. For instance, the level of x-ray energy emitted by a medical diagnostic imaging system may be measured in terms of radiation dosage. Periodic performance evaluation of medical diagnostic imaging systems ensures that the radiation dosage to which the target is exposed does not exceed regulatory standards.

Additionally, medical diagnostic imaging system performance may be monitored in order to determine which capabilities may be improved through further modification. If system parameters, such as network bandwidth or disk speed, do not meet performance specifications, performance data may be used to support changes to a medical diagnostic imaging system. Similarly, performance data may help isolate problems or defects to particular components or subsystems in a medical diagnostic imaging system. The detection of fluctuation in parameters, such as drive current, voltage, and temperature, may help to identify wear and to prevent future system failures.

Heretofore, medical diagnostic imaging systems have offered limited capabilities to carry out performance analysis. Current systems that collect medical diagnostic imaging system data must be pre-programmed with any and all desired parameter variables for which it is desirable to collect data (e.g., temperature, voltage, current, etc.). In order to change the amount or type of data collected for a medical diagnostic imaging system, a technician must manually reconfigure the system on-site or reprogram the software of the system. For example, if analysis of a first set of parameters (e.g., detector voltages and currents) indicates that the problem may be in a second set of parameters, the system must be manually reconfigured on-site. Manual reconfiguration may include rewriting the system's diagnostic or application software to include the second set of parameters.

In addition, conventional medical diagnostic imaging systems must be pre-programmed to collect data at a preset sampling rate (e.g., every patient, every minute, every second, etc.). Parameter variable data is collected and logged at a predetermined sampling rate or frequency. The sampling rate for data collection and logging can only be changed by a technician manually reconfiguring the system on-site. For example, in order to reduce or increase the amount of data being received for analysis, the system must be manually adjusted on-site. Manual adjustment of the sampling rate for a parameter variable may include modification of the system's diagnostic software.

On-site manual reconfiguration of the system unnecessarily complicates isolation and correction of errors in a medical diagnostic imaging system. Additionally, the necessity of on-site manual reconfiguration by a technician increases the amount of time, money, and personnel needed to perform accurate error detection.

Thus, a need has long existed for a system able to automatically log and analyze performance data for a medical diagnostic imaging system. Additionally, a need has long existed for a system that can be easily reconfigured to log and analyze different amounts or types of performance data for a medical diagnostic imaging system. Also, a need has long existed for a system that can log and analyze different characteristics of a chosen data set of a medical diagnostic imaging system. The preferred embodiments of the present invention address these needs and other concerns with past systems for analyzing medical diagnostic imaging systems.

BRIEF SUMMARY OF THE INVENTION

A method and system are provided for configurable logging and analysis of performance data for a medical diagnostic imaging system. A medical diagnostic imaging system may be divided into subsystems. The subsystems include data acquisition modules for acquiring desired types of data related to the performance of an associated subsystem. The data acquisition modules acquire raw performance data (e.g., temperature, current, voltage, etc.) during the operation of the medical diagnostic imaging system. The data acquisition modules may remotely acquire the raw performance data. The raw performance data is acquired based upon a configuration file which identifies parameters associated with a desired type of performance analysis. New configuration files may be remotely downloaded to dynamically select at least one parameter for a desired type of performance analysis. Parameters in the configuration file may comprise at least one of a performance variable and a sampling rate for the performance variable.

A processing module processes the raw performance data acquired by the data acquisition modules. Data may be processed in real-time during the operation of the medical diagnostic imaging system. The processing module produces characteristic data summarizing the raw performance data. For example, the processing module may calculate trend statistics or perform statistical analyze on the raw performance data to produce characteristic data. Characteristic data may include at least one of minimum value, maximum value, mean, standard deviation and the like. An output module outputs the characteristic data identifying the performance of the medical diagnostic imaging system. The output module may output the characteristic data to at least one of a storage buffer, trending log, display, and central processing system.

These and other features of the preferred embodiments of the present invention are discussed or apparent in the following detailed description of the preferred embodiments of the present invention.

DETAILED DESCRIPTION OF THE INVENTION

Figure 1:
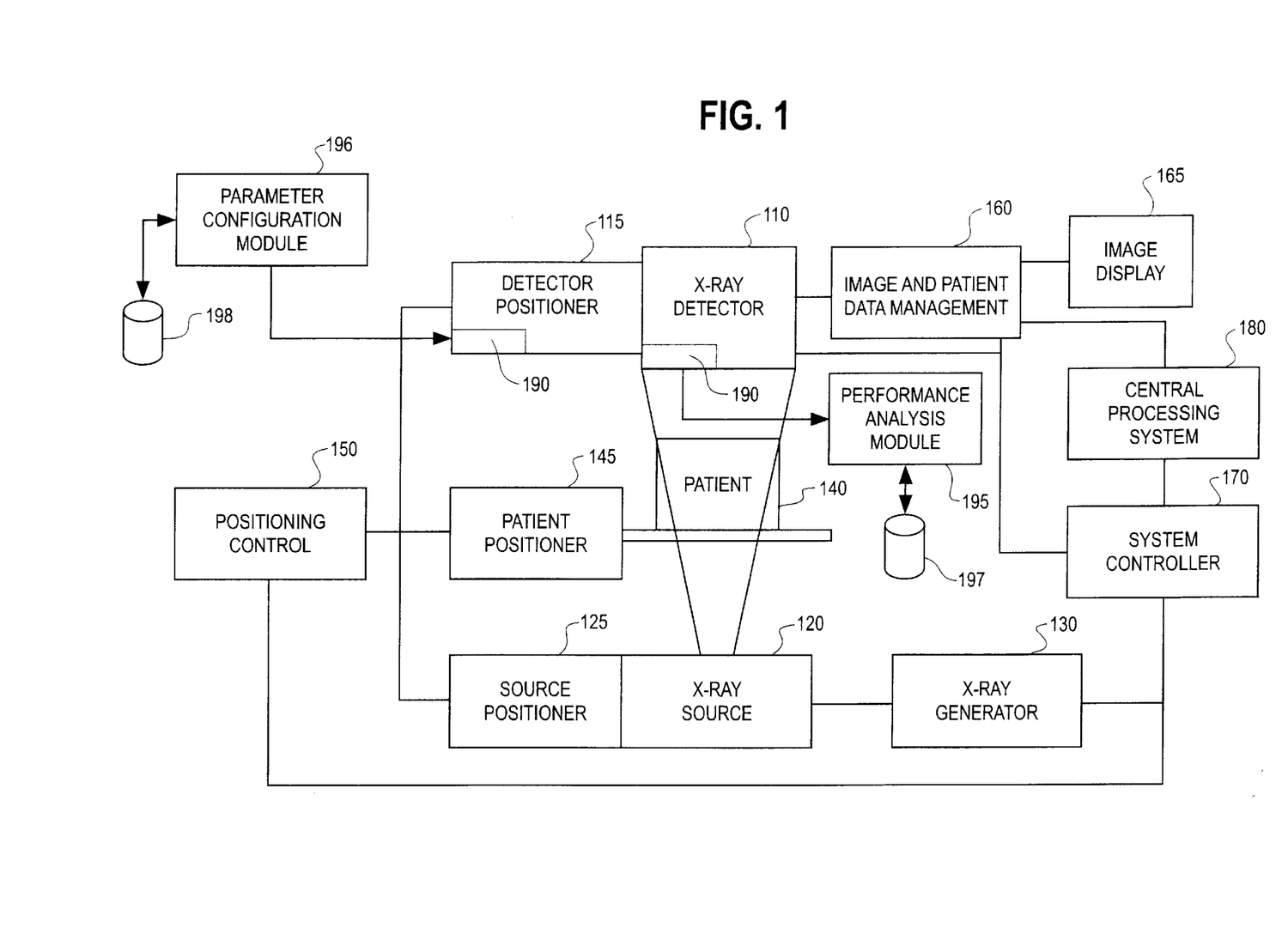
FIG. 1 illustrates a preferred embodiment of a general medical diagnostic imaging system used in connection with the present invention.

FIG. 1 illustrates a preferred embodiment of a medical diagnostic imaging system 100 used in accordance with the present invention. The medical diagnostic imaging system 100 includes a plurality of subsystems. For purposes of illustration only, the medical diagnostic image system is described as an x-ray system. The medical diagnostic imaging system 100 includes subsystems, such as an x-ray detector 110, a detector positioner 115, an x-ray source 120, a source positioner 125, an x-ray generator 130, a patient 140, a patient positioner 145, a positioning control 150, an image and patient data management module 160, an image display 165, a system controller 170, and a central processing system 180. The medical diagnostic imaging system 100 also includes a performance analysis module 195, a parameter configuration module 196, a trending log database 197 and file storage medium 198. Each subsystem of a medical diagnostic imaging system 100 may include a data acquisition module 190.

The data acquisition modules 190 acquire raw performance data during operation of the medical diagnostic imaging system 100 and provide the raw performance data to the performance analysis module 195. The performance analysis module 195 processes the raw performance data in real time during operation of the medical diagnostic imaging system 100 to produce characteristic data summarizing the raw performance data of associated subsystems. The performance analysis module 195 also outputs the characteristic data identifying the performance of the medical diagnostic imaging system 100. The performance analysis module 195 may store in a buffer the characteristic data. Alternatively, the performance analysis module 195 may log the characteristic data in a trending log, or display the characteristic data and/or transmit the characteristic data to a central processing system 180. The trending log may be stored in a database 197, in the central processor 180 or elsewhere. The performance analysis module 195 calculates trend statistics as characteristic data based on the raw performance data. The calculation of trending statistics may include calculating at least one of the minimum value, maximum value, mean, standard deviation and the like of the raw performance data as characteristic data.

The raw performance data may be categorized into different parameter classes, for example voltage, temperature, image quality, performance, wear parts, usage and the like. The voltage parameter class may represent one or more voltage values obtained from the various subsystems by one or more data acquisition modules 190. By obtaining voltage data from one or more subsystems, the performance analysis module 195 may generate characteristic data sets for the voltage parameter class evidencing voltage fluctuations throughout the system. A user may analyze such voltage fluctuations to detect faults or analyze performance.

Temperature parameters may be monitored in various subsystems as a class in order to determine if thermal fluctuations are due to environment or system usage and the like. The image quality parameter provides raw performance of data related to image quality, such as tube output and the like. The performance parameter class represents raw performance data for network bandwidth, disc speed and the like. The performance parameter class may be of interest when the system is not executing at a desired speed. Inferior performance may be caused by intermittent time outs or exceeding performance specifications or the like. The wear parts parameter class includes raw performance data related to the measurement of mechanical and electrical wear upon parts. By way of example, the raw performance data related to part wear may correspond to drive currents obtained throughout the subsystems, such as from rotor drive currents, filament drives and the like. By monitoring drive current, it may be possible to identify whether wear is causing excessive resistance, such as mechanical friction resistance or electrical resistance. The usage parameter class may be used to measure the system usage, such as the number of exposures or accumulated dose. Usage parameters represent independent trend variables and may be used to maintain a system history.

During operation, the performance analysis module 195 instructs each data acquisition module 190 to acquire raw performance data with respect to a desired number of parameters. The performance analysis module 195 further instructs the data acquisition modules 190 to obtain raw performance data at a predetermined data acquisition rate. By controlling the specific parameters and the data acquisition rate, the performance analysis module 195 is able to optimize temporal granularity of the raw performance data and long term coverage to summarize and trend logged raw performance data.

FIG. 1 further illustrates a parameter configuration module 196 which communicates with a configuration of file storage medium 198. The parameter configuration module 196 dynamically configures performance analysis of the medical diagnostic imaging system 100. As explained above, at least one of the subsystems within the medical diagnostic imaging system includes a data acquisition module 190 capable of acquiring raw performance data with respect to a plurality of parameters associated with performance of one or more subsystems. The parameter configuration module 196 dynamically selects at least one of the parameters based on a predefined parameter configuration associated with a corresponding type of performance analysis. The corresponding type of performance analysis may be user defined or automatically obtained from the configuration file storage medium 198.

More specifically, the configuration module 196 receives downloadable configuration files from the medium 198 or elsewhere identifying parameters associated with a desired type of performance analysis. The configuration module 196 selects a set of parameters associated with the desired type of performance analysis. Optionally, the parameter configuration module 196 may select multiple sets of parameters based upon corresponding multiple sets of parameter configurations and in turn separately defines operation of associated data acquisition modules 190.

Once the parameter configuration module 196 defines the parameters to be used within the data acquisition modules 190, associated raw performance data is provided from the data acquisition modules 190 to the performance analysis module 195 as explained above.

The patient 140 is positioned in the medical diagnostic imaging system 100 using the patient positioner 145. In one exemplary system, an x-ray source 120 is positioned below the patient 140 using the source positioner 125. The x-ray detector 110 is positioned above the patient 140 using the detector positioner 115. The positioning control 150 controls the positioning of the patient 140 between the x-ray source 120 and x-ray detector 110. The x-ray generator 130 produces the x-rays that are transmitted from the x-ray source 120 through the patient 140 to the x-ray detector 110.

The image and patient data management module 160 receives an image from the x-ray detector 110. The image and patient data management module 160 also receives data from subsystems 110, 115, 120, 125, 130, 145, 150, and 170 of the medical diagnostic imaging system 100. The image and patient data management module 160 transmits image data, patient data and system data to an image display 165. The image and patient data management module 160 also transmits the image data and patient data and system data to a central processing system 180. The central processing system 180 may direct the system controller 170 to adjust parameters of the subsystems 110, 115, 120, 125, 130, 145, 150 of the medical diagnostic imaging system 100.

Figure 2:
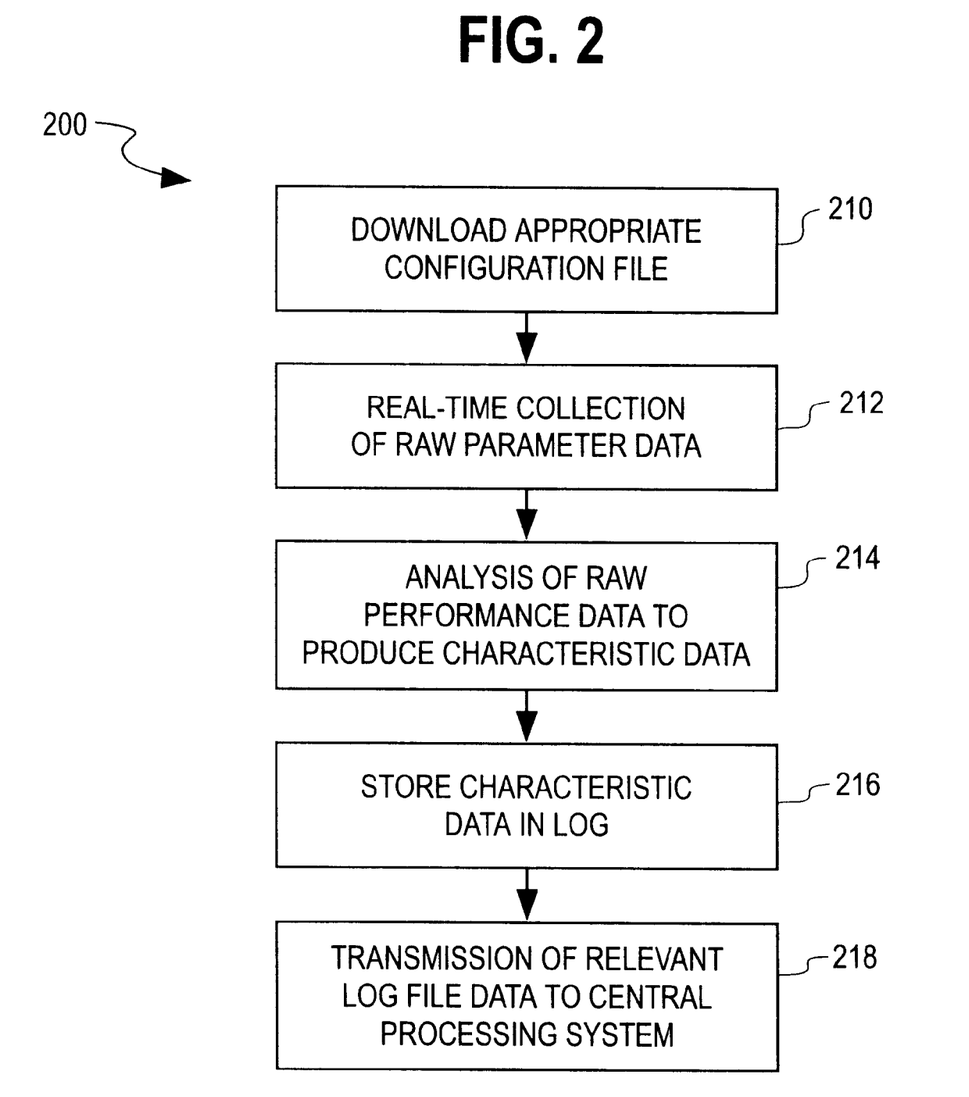
FIG. 2 illustrates a flowchart for configurable logging and analysis of medical diagnostic imaging system data according to a preferred embodiment of the present invention.

FIG. 2 illustrates a flowchart 200 for configurable logging and analysis of medical diagnostic imaging system data according to a preferred embodiment of the present invention. In step 210, a configuration file is downloaded from medium 198 or from a central processing system 180 to the parameter configuration module 1956 and/or to the performance analysis module 195. The downloaded configuration file contains a desired set of parameters, such as voltage, temperature, timing, image quality, performance, wear parts, usage and the like. A parameter may have at least one of a parameter variable and a sampling rate for that variable.

Based upon the parameters in the downloaded configuration file, at step 212, the performance analysis module 195 and data acquisition modules 190 perform real-time collection of raw performance data from one or more subsystems of the medical diagnostic imaging system 100. In step 214, an analysis engine in the, performance analysis module 195 analyzes the raw performance data to produce characteristic data. Characteristic data may include minimum, maximum, mean, average, standard deviation and the like. In step 216, the performance analysis module 195 stores the characteristic data in a log file in memory. In step 218, the performance analysis module 195 transmits relevant characteristic data in the log file to a central processing system 180.

Figure 3:
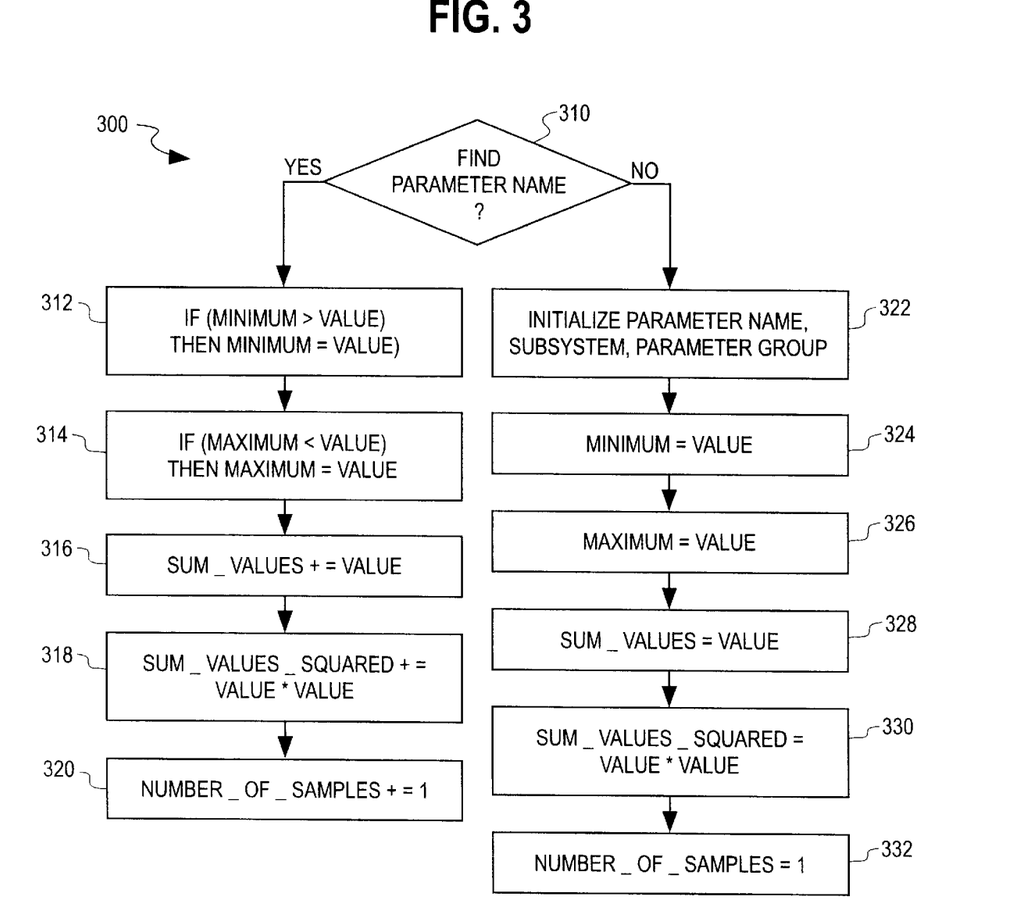
FIG. 3 illustrates a flowchart of a preferred embodiment of accumulating raw performance data of a medical diagnostic imaging system according to a preferred embodiment of the present invention.

FIG. 3 illustrates a flowchart 300 of a preferred embodiment for accumulating raw performance data of a medical diagnostic imaging system 100. In step 310, a data acquisition module 190 transmits data values for a selected parameter to the performance analysis module 195. The performance analysis module 195 searches for the parameter name in an internal database 197. If the parameter name is not found, in step 322, the performance analysis module 195 initializes a new entry to the database 197 with the parameter name, name of the medical diagnostic imaging subsystem from which the data values are obtained, and the name of the parameter group. In step 324, the performance analysis module 195 stores the data value as a minimum. In step 326, the performance analysis module 195 stores the same data value as a maximum. In step 328, the performance analysis module 195 sets a sum of values equal to the transmitted data value. Additionally, in step 330 and 332, the performance analysis module 195 equates a sum of values squared to the square of the transmitted value and a number of samples is initialized to one. In accordance with steps 322–332, the performance analysis module 195 initializes a characteristic data set for a particular, corresponding parameter.

If the parameter name associated with the incoming data value is found in the database 197, then the performance analysis module 195 updates the characteristic data for the identified parameter in the database 197. In step 312, the performance analysis module 195 compares the transmitted data value to the stored minimum value. If the stored minimum value for the corresponding parameter is greater than the transmitted data value, then the transmitted new data value is stored as the new minimum value. In step 314, the performance analysis module 195 compares the transmitted new data value to the stored maximum value. If the stored maximum value is less than the transmitted new data value, then the transmitted data value is stored as the new maximum value. The transmitted data value is added to the stored sum of values in step 316. In step 318, the performance analysis module 195 squares the transmitted data value and adds the squared data value to the stored sum of values squared. In step 320, the number of samples is incremented by one.

Figure 4:
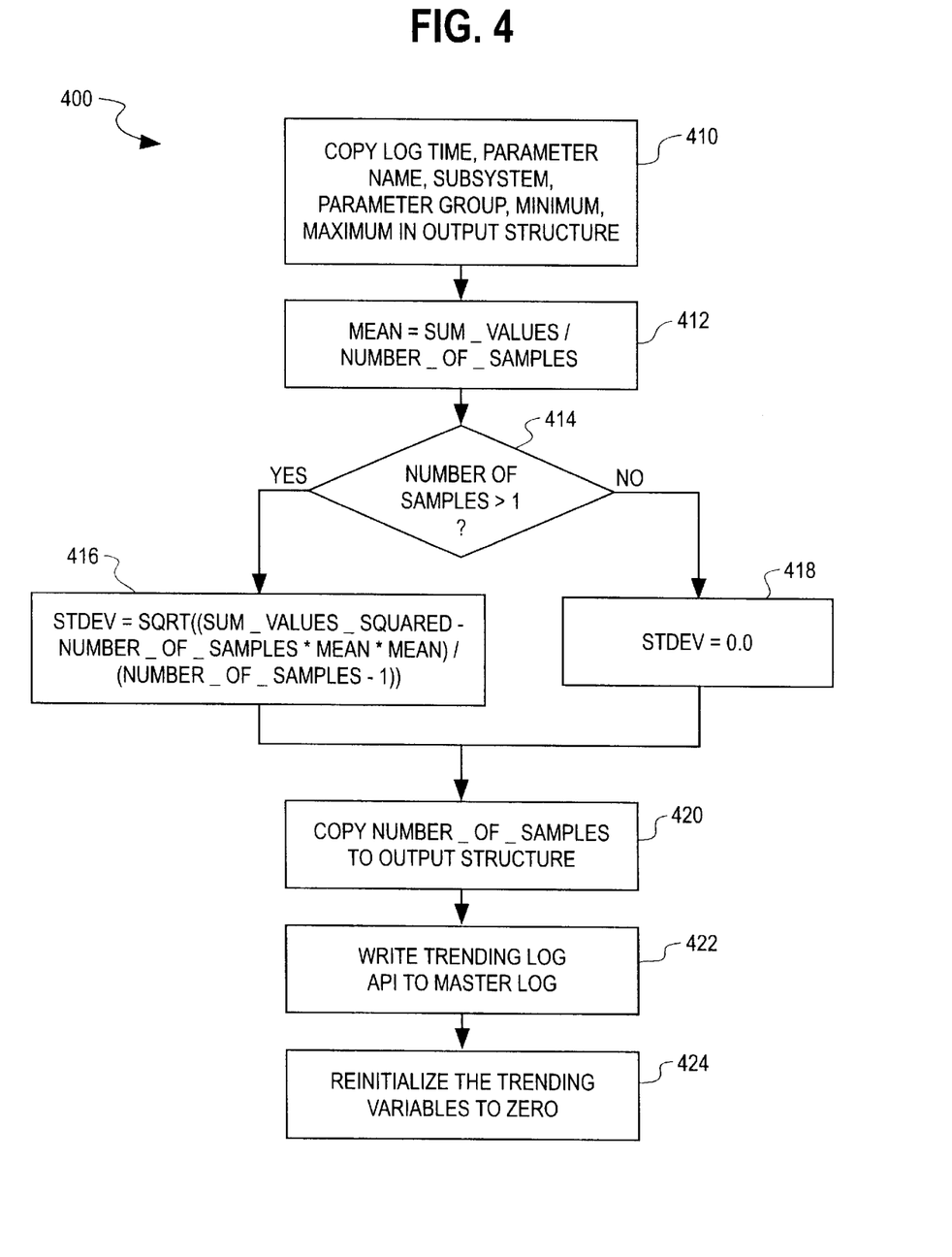
FIG. 4 illustrates a flowchart of a preferred embodiment of logging of characteristic data of a medical diagnostic imaging system 100 according to a preferred embodiment of the present invention.

FIG. 4 illustrates a flowchart 400 of a preferred embodiment for logging of characteristic data of a medical diagnostic imaging system 100. In step 410, for each of the relevant characteristic data, the performance analysis module 195 copies the time of logging, the parameter name, the name of the medical diagnostic imaging subsystem, the name of the parameter group, the minimum value, the maximum value and the like into an output structure. In step 412, the performance analysis module 195 calculates a mean value by dividing the sum of values by the number of samples. In step 414, the performance analysis module 195 determines whether the number of samples for the parameter name is greater than one. If the number of samples is greater than one, then in step 416, a standard deviation is calculated from the following equation:

$$StDev = SQRT\left(\frac{Sum\_Values\_Squared - Number\_of\_Samples \times Mean \times Mean}{Number\_of\_Samples - 1}\right)$$

If the number of samples is equal to one, then in step 420 the standard deviation is set to 0.0. In step 422, the performance analysis module 195 copies the mean, standard deviation, and number of samples to the output structure. In step 422, the performance analysis module 195 writes the output structure to a central trending log such as in database 197 or central processing system 180. In step 424, the performance analysis module 195 reinitializes trending variables, such as sum of values, sum of values squared, and number of samples, to zero.

Figure 5:
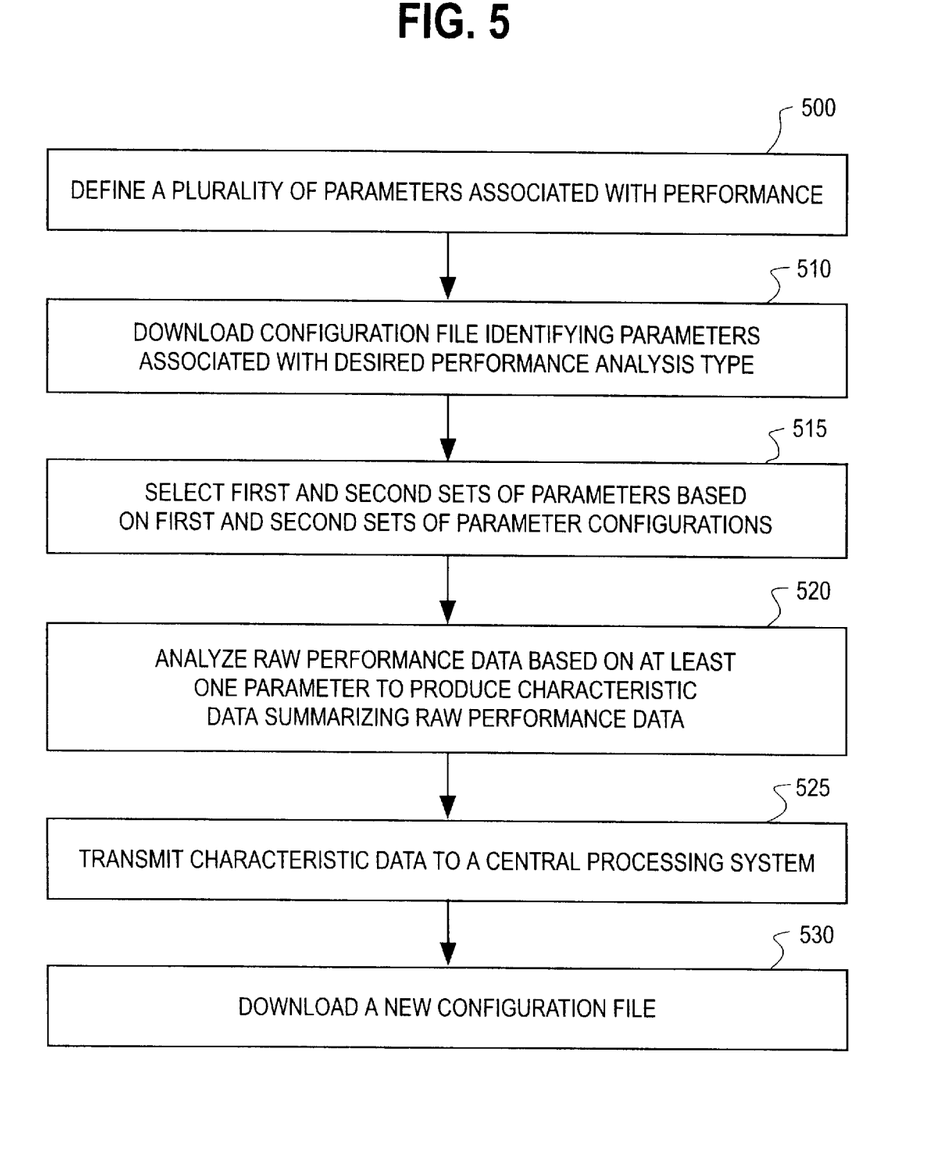
FIG. 5 illustrates a flow chart of a preferred embodiment of a flow chart setting forth the processing sequence for dynamically configuring the performance analysis of a medical diagnostic imaging system in accordance with a preferred embodiment of the present invention.

FIG. 5 illustrates an alternative embodiment for dynamically configuring performance analysis of the medical diagnostic imaging system 100. In the embodiment of FIG. 5, the parameter configuration module 196 defines a plurality of parameters associated with performance of the medical diagnostic imaging system (step 500). Exemplary parameters have been discussed above. Next, at step 510, the system dynamically selects at least one of the parameters based on a defined parameter configuration associated with a corresponding desired type of performance analysis. For example, at step 510, the parameter configuration module may download a configuration file from the central processing system 180 or from the configuration file storage medium 198. The configuration file identifies parameters associated with a desired type of performance analysis. The type of performance analysis may be automatically selected or manually selected by a user or remotely selected via an internet correction and the like. At step 515, the parameter configuration module 196 selects first and second sets of parameters based on first and second sets of parameter configurations. The parameters may comprise a performance variable and a sampling rate for the performance variable. The first an second sets of parameters may correspond to a first and second subsystems, first and second classes of parameters, first and second sampling rates of a single class of parametric and the like. Exemplary performance variables have been discussed above.

At step 520, the performance analysis module 195 analyzes the raw performance data based on at least one parameter to produce characteristic data summarizing the raw performance data. Exemplary analyses are discussed above. At step 525, the performance analysis module 195 transmits the characteristic data to a central processing system 180. At step 530, the parameter configuration module 196 downloads a new configuration file and repeats the process of steps 510–525.

The preferred embodiment of the present invention may be useful in many situations involving medical diagnostic imaging systems. For example, suppose an x-ray system is producing low quality images. First, the system may download a configuration file from a central processing system to examine parameter variables at an infrequent sampling rate from x-ray detector 110, detector positioner 115, x-ray source 120, source positioner 125, x-ray generator 130, patient positioner 145, the positioning control 150, and system controller 170. The initial set of raw performance data is collected by the image and patient data management module 160. After analyzing the raw performance data, the error may be localized to the x-ray detector 110. A new configuration file may be downloaded from the central processing system which examines only the parameters of the x-ray detector 110 at an accelerated sampling rate. When the new performance data is analyzed, numbers may indicate that a problem exists with the voltage of the x-ray detector 110. Another configuration may concentrate solely on the voltage parameter of the x-ray detector 110 and collect samples at a high sampling rate to accurately pinpoint the problem.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features which come within the spirit and scope of the invention.

What is claimed is:

1. A method for logging information related to the performance of a medical diagnostic imaging system, comprising:

acquiring raw performance data during operation of the medical diagnostic imaging system;

processing said raw performance data in real time during operation of said medical diagnostic imaging system to produce characteristic data summarizing said raw performance data; and outputting said characteristic data identifying the performance of the medical diagnostic imaging system.

2. The method of claim 1 wherein said outputting step further comprises at least one of the steps of storing in a buffer, logging to a trending log, displaying, and transmitting to a central processing system.

3. The method of claim 1 wherein said processing step includes calculating trend statistics as said characteristic data based on said raw performance data.

4. The method of claim 1 wherein said processing step further comprises calculating at least one of minimum value, maximum value, mean, and standard deviation as said characteristic data.

5. The method of claim 1 wherein said processing step further comprises accumulating predefined parameter values from said raw performance data.

6. The method of claim 1 wherein said characteristic data produced by processing step includes statistical data based on statistical analysis of said raw performance data.

7. The method of claim 1 wherein said acquiring step further comprises remote acquisition of said raw performance data.

8. The method of claim 1, wherein said raw performance data relates to medical diagnostic imaging system configuration information.

9. The method of claim 1, wherein said raw performance data includes at least one of temperature, current, voltage, image quality, performance, usage, wear, and dosage.

10. The method of claim 1, wherein said raw performance data is acquired from said medical diagnostic imaging system while said medical diagnostic imaging system simultaneously acquires image data from a target.

11. An apparatus for logging information related to the performance of a medical diagnostic imaging system comprising:

at least one medical diagnostic imaging subsystem having at least one parameter associated with performance of said subsystem; and an acquisition module dynamically acquiring raw performance data during operation of the medical diagnostic imaging subsystem;

a processing module processing said raw performance data in real time during operation of said medical diagnostic imaging subsystem to produce characteristic data summarizing said raw performance data; and an output module outputting said characteristic data identifying the performance of the medical diagnostic imaging subsystem.

12. The apparatus of claim 11 wherein said acquisition module enables the remote dynamic acquisition of raw performance data during operation of the medical diagnostic imaging system.

13. The apparatus of claim 11 wherein said output module comprises at least one of a storage buffer, trending log, display, and central processing system.

14. The apparatus of claim 4 wherein said processing module includes a trending statistics engine that calculates trend statistics as said characteristic data based on said raw performance data.

15. The apparatus of claim 4 wherein said processing module calculates at least one of minimum value, maximum value, mean, and standard deviation as said characteristic data based on said raw performance data.

16. The apparatus of claim 11 wherein said processing module accumulates predefined parameter values from said raw performance data.

17. The apparatus of claim 11 wherein said processing module produces statistical data as said characteristic data based on statistical analysis of said raw performance data.

18. The method of claim 11, wherein said raw performance data relates to medical diagnostic imaging system configuration information.

19. The method of claim 11, wherein said raw performance data includes at least one of temperature, current, voltage, image quality, performance, usage, wear, and dosage.

20. The method of claim 11, wherein said acquisition module acquires said raw performance data from said medical diagnostic imaging system while said medical diagnostic imaging system simultaneously acquires image data from a target.

21. A method for dynamically configuring performance analysis of a medical diagnostic imaging system comprising:

defining a plurality of parameters associated with performance of a medical diagnostic imaging system; and dynamically selecting at least one of said parameters based on a defined parameter configuration associated with a corresponding type of performance analysis.

22. The method of claim 21 wherein said selecting step further comprises downloading a configuration file identifying parameters associated with a desired type of performance analysis.

23. The method of claim 21 wherein said selecting step further comprises selecting a first set of parameters and a second set of parameters based on first and second sets of parameter configurations.

24. The method of claim 21 wherein said at least one of said parameters comprises at least one of a performance variable and a sampling rate for said performance variable.

25. The method of claim 21 further comprising:

analyzing raw performance data based on said at least one parameter to produce characteristic data summarizing said raw performance data.

26. The method of claim 25 wherein said analyzing step performs a first analysis based on a first set of at least one parameter and performs a second analysis based on a second set of a least one parameter.

27. The method of claim 25 further comprising:

transmitting said characteristic data to a central processing system; and downloading a second configuration file.

28. The method of claim 25, wherein said raw performance data is obtained from said medical diagnostic imaging system while said medical diagnostic imaging system simultaneously acquires image data from a target.

29. The method of claim 21, wherein said plurality of parameters include at least one of temperature, current, voltage, image quality, performance, usage, wear, and dosage.

30. An apparatus for dynamically configuring performance analysis of a medical diagnostic imaging system comprising:

at least one medical diagnostic imaging subsystem having a plurality of parameters associated with performance of said subsystem; and a configuration module for dynamically selecting at least one of said parameters based on a defined parameter configuration associated with a corresponding type of performance analysis.

31. The apparatus of claim 30 wherein said configuration module further comprises a downloadable configuration file identifying parameters associated with a desired type of performance analysis.

32. The apparatus of claim 30 wherein said configuration module selects a first set of parameters and a second set of parameters based on first and second sets of parameter configurations.

33. The apparatus of claim 30 wherein said configuration module selects a first set of parameters based on a first parameter configuration associated with a first subsystem and selects a second set of parameters based on a second parameter configuration associated with a second subsystem.

34. The apparatus of claim 30 further comprising a performance analysis module that performs analysis based on said at least one of said parameters.

35. The apparatus of claim 30 further comprising a performance analysis module that performs a first analysis based on a first set of at least one parameter and performs a second analysis based on a second set of at least one parameter.

36. The apparatus of claim 30 wherein said at least one of said parameters comprises at least one of a performance variable and a sampling rate for said performance variable.

37. The apparatus of claim 30, wherein said plurality of parameters include at least one of temperature, current, voltage, image quality, performance, usage, wear, and dosage.

38. The method of claim 30, wherein said performance analysis is based on raw performance data obtained during acquisition of an image by said at least one medical diagnostic imaging subsystem.

39. A method for dynamically calibrating a medical diagnostic imaging system, said method comprising:

accessing a configuration file comprising configuration information for a medical diagnostic imaging system;

obtaining and analyzing raw performance data during operation of said medical diagnostic system; and remotely calibrating said medical diagnostic imaging system based on a relationship between said configuration information and said raw performance data.

40. The method of claim 39, wherein said raw performance data includes at least one of temperature, current, voltage, image quality, performance, usage, wear, and dosage.

41. The method of claim 39, wherein said raw performance data is acquired from said medical diagnostic imaging system while said medical diagnostic imaging system simultaneously acquires image data from a target.

42. A method for real-time collection of raw performance data, said method comprising:

remotely accessing a medical imaging system;

accumulating raw performance data during operation of the medical imaging system, said raw performance data including at least one of temperature, current, voltage, image quality, performance, usage, wear, and dosage; and storing said raw performance data in a trending log.

43. The method of claim 42 further comprising:

analyzing said raw performance data in said trending log; and reconfiguring said medical imaging system using said raw performance data from said trending log.

44. The method of claim 42, wherein said raw performance data relates to medical imaging system configuration information.

45. The method of claim 42, wherein said raw performance data is accumulated from said medical imaging system while said medical imaging system simultaneously acquires image data from a target.

46. A method of locating problems in a medical imaging system, said method comprising:

collecting raw performance data during operation of a medical imaging system; and analyzing fluctuations in said raw performance data to locate problems in said medical imaging system.

47. The method of claim 46, wherein said raw performance data relates to medical diagnostic imaging system configuration information.

48. The method of claim 46, wherein said raw performance data includes at least one of temperature, current, voltage, image quality, performance, usage, wear, and dosage.

49. The method of claim 31, wherein said raw performance data is collected from said medical imaging system while said medical imaging system simultaneously acquires an image.

* * * * *